United States Patent [19]

Edlund

[11] Patent Number: 5,259,870
[45] Date of Patent: Nov. 9, 1993

[54] HYDROGEN-PERMEABLE COMPOSITE METAL MEMBRANE

[75] Inventor: David J. Edlund, Bend, Oreg.

[73] Assignee: Bend Research, Inc., Bend, Oreg.

[21] Appl. No.: 986,692

[22] Filed: Dec. 7, 1992

Related U.S. Application Data

[63] Continuation-in-part of Ser. No. 566,092, Aug. 10, 1990, abandoned.

[51] Int. Cl.⁵ ........................ B01D 53/22; B01D 71/02
[52] U.S. Cl. ............................................. 95/56; 96/11; 55/524
[58] Field of Search .................... 55/16, 158, 68, 524

[56] References Cited

U.S. PATENT DOCUMENTS

| | | | |
|---|---|---|---|
| 2,958,391 | 11/1960 | de Rosset | 55/158 X |
| 3,241,298 | 3/1966 | Pierce | 55/16 X |
| 3,344,582 | 10/1967 | Merrill et al. | 55/16 |
| 3,350,846 | 11/1967 | Makrides et al. | 55/16 |
| 3,393,098 | 6/1968 | Hartner . | |
| 3,413,777 | 12/1968 | Langley et al. | 55/158 |
| 3,428,476 | 2/1969 | Langley et al. | 55/16 X |
| 3,447,288 | 6/1969 | Juda et al. | 55/158 |
| 4,388,479 | 6/1983 | Gryaznov | 568/828 |
| 4,468,235 | 8/1984 | Hill | 55/16 |
| 4,496,373 | 1/1985 | Behr et al. | 55/16 |
| 4,528,003 | 7/1985 | Dittrich et al. | 55/158 |
| 4,536,196 | 8/1985 | Harris | 55/16 |
| 4,655,797 | 4/1987 | Iniotakis et al. | 55/16 |
| 4,699,637 | 10/1987 | Iniotakis et al. | 55/16 X |
| 4,810,485 | 3/1989 | Marianowski et al. | 55/16 X |
| 4,865,630 | 9/1989 | Abe | 55/158 |
| 4,944,777 | 7/1990 | Shmayda et al. | 55/16 |

FOREIGN PATENT DOCUMENTS

| | | | |
|---|---|---|---|
| 60-071003 | 4/1985 | Japan | 55/158 |
| 61-138516 | 6/1986 | Japan | 55/158 |
| 62-027005 | 2/1987 | Japan | 55/158 |
| 62-121616 | 6/1987 | Japan | 55/158 |
| 62-273029 | 11/1987 | Japan | 55/158 |
| 62-273030 | 11/1987 | Japan | 55/158 |
| 63-004829 | 1/1988 | Japan | 55/158 |
| 63-229122 | 9/1988 | Japan | 55/158 |
| 1-004216 | 1/1989 | Japan | 55/158 |
| 1058587 | 12/1983 | U.S.S.R. | 55/158 |

OTHER PUBLICATIONS

Houldcroft, "Welding Processes", p. 3, (1975).
Science and Invention Encyclopedia, vol. 20, p. 2654, (1977).

*Primary Examiner*—Robert Spitzer
*Attorney, Agent, or Firm*—Chernoff, Vilhauer, McClung & Stenzel

[57] ABSTRACT

Novel composite metal membranes are disclosed that contain an intermetallic diffusion barrier separating a hydrogen-permeable base metal and a hydrogen-permeable coating metal.

17 Claims, 1 Drawing Sheet

HYDROGEN-PERMEABLE COMPOSITE METAL MEMBRANE

The government has rights in this invention pursuant to Grant No. ISI-8722212 awarded by the National Science Foundation.

This is a continuation-in-part of application Ser. No. 07/566,092 filed Aug. 10, 1990, now abandoned.

BACKGROUND OF THE INVENTION

Metal membranes that are selectively permeable to hydrogen are known. See, for example, U.S. Pat. Nos. 4,388,479 and 3,393,098, both of which disclose Group V and VIII alloy membranes such as palladium alloy catalytic membranes. The prohibitively high cost of palladium has lead to efforts to fabricate composite hydrogen-permeable metal membranes by coating certain transition metal alloy base metals with palladium or palladium alloys. See, for example, U.S. Pat. Nos. 4,468,235 and 3,350,846. The coating on such base metals imparts chemical resistance to the base metal and in some cases increases the rate of adsorption of hydrogen onto the metal membrane surface. However, such coated metal membranes have an inherent shortcoming in that, under the elevated temperature conditions of use, the coating metal tends to diffuse into the base metal, thereby destroying the benefits available from such composite metal membranes. U.S. Pat. No. 4,496,373 discloses a nonporous hydrogen-permeable composite metal membrane that addresses this intermetallic diffusion problem for a base metal alloy of a specific composition coated with a palladium alloy of specific composition. However, the composition of the palladium alloy coating and the base metal alloy are narrowly defined so as to favor partitioning of the palladium into the coating alloy as opposed to the base metal alloy. Consequently, this approach is not general in nature, requires strict control over alloy composition, and allows for little variation in selection of metals for membrane fabrication.

These and other shortcomings of prior art hydrogen-permeable composite metal membranes are overcome by the present invention, which is summarized and described in detail below.

SUMMARY OF THE INVENTION

The present invention provides a novel nonporous composite hydrogen-permeable, hydrogen-selective, and stable metal membrane and method of using the same for the selective separation of hydrogen from other gases. The essential structure of the membrane comprises a hydrogen-permeable base metal and a hydrogen-permeable coating metal separated by a hydrogen-permeable intermetallic diffusion barrier. The membrane retains at least 20% of the initial hydrogen flux after several days' operation at high temperatures.

DETAILED DESCRIPTION OF THE INVENTION

The composite membrane of the present invention is selectively permeable to hydrogen gas and may be used in conventional fashion to separate hydrogen from other gases such as nitrogen, carbon monoxide, carbon dioxide, methane, ethane, propane, steam or ammonia by methods known in the art, the essential features of which comprise contacting a feed gas containing hydrogen and other gases at temperatures generally exceeding 500° C., allowing the selective permeation of hydrogen through the composite membrane, and collecting the permeated hydrogen. The hydrogen selectivity of the composite membrane is outstanding, exhibiting a selectivity of $\geq 100$ with a flux of $\geq 0.03$ m$^3$/m$^2$·hr at 700° C. and 100 psig feed side pressure with the permeate side at ambient pressure.

The composite membrane of the present invention is particularly stable under conditions of elevated temperature. Specifically, when exposed to a 100 psig hydrogen feed stream of $\geq 99.999\%$ purity at $\geq 500°$ C., and ambient pressure on the permeate side, the composite membrane retains $\geq 20\%$ of its initial flux over a continuous period of operation of 100 hours and even up to two weeks. As shown herein, this stability is directly attributable to the presence of the intermetallic diffusion barrier.

The base metal of the metal membrane of the present invention is selected from hydrogen-permeable transition metals from Groups IIIB, IVB, VB, VIIB and VIIIB of the periodic table and alloys containing $\geq 20$ wt % of said metals, and may be from 25 to 250 microns in thickness.

The coating metal is a hydrogen-permeable transition metal that is chemically and physically stable at temperatures of at least 500° C., is preferably selected from the transition metals of Groups VIIB and VIIIB of the periodic table, most preferably Fe, Mn, Ni, Pd, Pt, Ru and alloys containing $\geq 20$ wt % of said metals, and preferably from 0.01 to 1.0 micron in thickness.

The intermetallic diffusion barrier is preferably selected from the group consisting essentially of oxides of aluminum, lanthanum, molybdenum, silicon, tungsten and yttrium, and sulfides of molybdenum, tungsten and vanadium, and may be from 0.1 to 25 microns in thickness. The intermetallic diffusion barrier is chemically stable under operating conditions (temperatures of at least 500° C.) with respect to reduction of the oxide or sulfide by either hydrogen or the base metal. The intermetallic diffusion barrier is applied as a continuous layer between the coating metal and the base metal and serves to greatly reduce interdiffusion between the coating metal and base metal of all chemical elements other than hydrogen.

Figure 1:
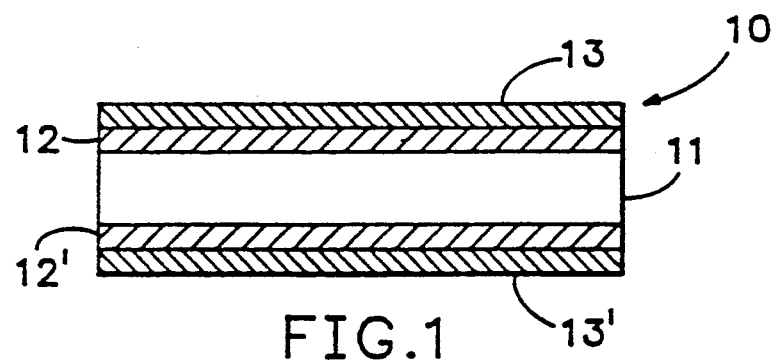
FIG. 1 is a schematic cross-sectional view of an exemplary composite membrane of the present invention.

Referring to FIG. 1, there is shown a preferred exemplary embodiment of a composite metal membrane 10 comprising a base metal layer 11, two intermetallic diffusion barrier layers 12 and 12' and two coating layers 13 and 13'. Although two layers 12 and 12' and 13 and 13' are shown, composite metal membranes having only single layers 12 and 13 also comprise useful embodiments of the present invention.

Figure 2:
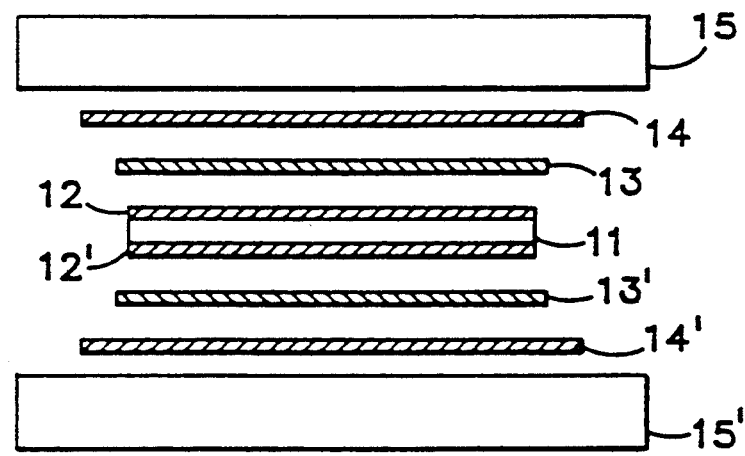
FIG. 2 is a schematic cross-sectional exploded view of an exemplary method of making the composite membrane of the present invention.

Fabrication of the composite metal membranes of the present invention is preferably by a temperature/pressure lamination of the three components. FIG. 2 schematically illustrates such a fabrication technique. In FIG. 2, there is shown an exploded cross-sectional view of the composite metal membrane of FIG. 1 prior to lamination, and wherein like numerals correspond to the same elements. In FIG. 2 there are shown graphite gaskets 14 and 14' and stainless steel press plates 15 and 15'. The graphite gaskets 14 and 14, seal the membrane against exposure to air during the lamination in order to protect against oxidation. The intermetallic diffusion barrier is preferably first applied chemically to the base metal by deposition thereon of an inorganic oxide or sulfide layer. In the case of oxides, the base metal may be coated by spraying, spinning or dipping with a solution of a precursor to the oxide, such as $SiCl_4$ (or $Si(OMe)_4$ with a catalytic amount of concentrated HCl), $WCl_6$ or $MoCl_5$, or alkoxides of Al, La, or Y, which then hydrolyzes to form the oxide layer. In the case of metal sulfide layers, the base metal may be simply exposed to a sulfide gas, such as hydrogen sulfide, at elevated pressure and temperature for a short time, such as 5 to 15 minutes. Alternatively, the base metal may be coated by spraying, spinning, or dipping with a solution of a precursor to the sulfide, such as $WCl_6$, $MoCl_5$ or $VCl_3$, which may then be reacted with hydrogen sulfide to form the sulfide layer. Yet another method for applying the oxide or sulfide layer is by vapor deposition of the desired oxide or sulfide onto the base metal.

EXAMPLE 1

A $Ni/SiO_2/V$ composite metal membrane was made using the following procedure. A vanadium disc, 5 cm in diameter and 152 microns thick, served as the base metal, providing good mechanical properties to the composite membrane. Six-micron-thick nickel foil served as the coating material, providing chemical inertness to the composite membrane. A thin layer of $SiO_2$ between the vanadium and nickel essentially prevented diffusion of the nickel coating into the vanadium base metal.

To fabricate the composite metal membrane, a thin layer of $SiO_2$ was deposited on both sides of the vanadium by dip-coating the vanadium disc with a 1M solution of $SiCl_4$ in methylene chloride at room temperature. As the methylene chloride solvent evaporated, the $SiCl_4$ rapidly hydrolyzed in the presence of atmospheric moisture to yield a film of $SiO_2$ approximately 25 microns thick. Good adhesion between the $SiO_2$ layer and the vanadium was observed. Next, the $SiO_2$-coated vanadium was laminated with the nickel foil at 700° C. under 20,000 pounds of pressure for 4 hours as shown schematically in FIG. 2 to produce the composite membrane. The composite membrane so prepared was flexible, and showed no sign of delamination when bent.

Average hydrogen flux through the composite membrane was measured at 700° C. using a 99.999% pure hydrogen gas feed stream at 100 psig (690 kPa), the permeated hydrogen being at ambient pressure. For comparison, the average hydrogen flux through a control membrane made by laminating the same thickness of nickel foil directly to the same thickness of vanadium without the use of an intervening $SiO_2$ layer was measured under identical conditions. The resulting average hydrogen flux in units of $m^3/m^2 \cdot hr$ are given in the table below for the initial flux and after 50 hours of operation.

| Membrane | Flux (initial) | Flux (50 hrs) | % Initial Flux |
|---|---|---|---|
| $Ni/SiO_2/V$ | 0.9 | 0.6 | 67 |

-continued

| Membrane | Flux (initial) | Flux (50 hrs) | % Initial Flux |
|---|---|---|---|
| Ni/V | 0.15 | 0.006 | 4 |

For this composite membrane, the layer that has the greatest resistance to hydrogen permeation (i.e., the layer that has the lowest hydrogen permeability) is the thin nickel coating (the limiting hydrogen flux through a nickel membrane 5 cm in diameter and 25 microns thick is $0.9 \ m^3/m^2 \cdot hr$). Since the observed rate of hydrogen permeation through the composite membrane cannot exceed the rate of permeation through each chemically distinct layer of the membrane, the nickel coating of the $Ni/SiO_2/V$ membrane limits the overall hydrogen flux.

As this Example shows, the $Ni/SiO_2/V$ composite metal membrane shows higher flux and longer lifetime (retaining 67% of the initial flux) than the Ni/V control membrane (which retained only 4% of the initial flux) indicating that the $SiO_2$ metal diffusion barrier is effective at preventing excessive decline in hydrogen flux. There is no such barrier in the Ni/V control membrane and, consequently, a marked decline in flux results.

EXAMPLE 2

A $NiCu/SiO_2/V$ composite metal membrane was made as follows. A vanadium disc, 5 cm in diameter and 152 microns thick, served as the base metal. NiCu foil (20 wt % Ni, 80 wt % Cu) 31 microns thick (made by laminating a 6-micron Ni foil to a 25-micron Cu foil) served as the coating material, providing chemical inertness to the composite membrane. A thin ($\leq 25$ microns) layer of $SiO_2$ between the vanadium and the NiCu coating served as the intermetallic diffusion barrier, and was deposited on both sides of the vanadium by spin coating the vanadium with a 1M solution of $Si(OMe)_4$ in methanol containing a catalytic amount of concentrated HCl. The $SiO_2$-coated vanadium was laminated with the NiCu foil in substantially the same manner as in Example 1 with substantially the same results.

Average hydrogen flux through the so-fabricated composite membrane was measured in the same manner as in Example 1. For comparison, the average hydrogen flux through a control membrane made by laminating the same thickness of NiCu foil directly to the same thickness of vanadium without the use of an intervening $SiO_2$ layer was measured under identical conditions. The results are given in the table below after 72 hours of operation.

| Membrane | Flux (initial) | Flux (72 hrs) | % Initial Flux |
|---|---|---|---|
| $NiCu/SiO_2/V$ | 2.4 | 2.4 | 100 |
| NiCu/V | 0.6 | 0.06 | 10 |

As is apparent, the composite metal membrane showed higher flux and longer lifetime than the NiCu/V control membrane.

EXAMPLE 3

A Ni/V-sulfide/V composite metal membrane was made as follows. A vanadium disc, 5 cm in diameter and 152 microns thick, served as the base metal, while a 6-micron-thick Ni foil served as the coating material. A thin layer of vanadium sulfide served as the intermetallic diffusion barrier, which was deposited on both sides of the vanadium by exposing the vanadium disc to 30 psig $H_2S$ at 700° C. for 10 minutes. Good adhesion between the vanadium sulfide layer and the vanadium was observed. The vanadium sulfide-coated vanadium was then laminated with the Ni foil at 700° C. under 20,000 pounds of pressure for 4 hours.

The average hydrogen flux through the composite membrane was measured in the same manner as in Example 1 and compared with the average hydrogen flux through a control membrane made by laminating the same thickness of Ni foil directly to the same thickness of vanadium under identical conditions without the use of an intervening sulfided-vanadium layer. The results after 50 hours of operation are given in the table below.

| Membrane | Flux (initial) | Flux (50 hrs) | % Initial Flux |
| --- | --- | --- | --- |
| Ni/V-sulfide/V | 0.062 | 0.046 | 74 |
| Ni/V | 0.14 | 0.004 | 3 |

As is apparent, the composite membrane showed higher flux and longer lifetime than the Ni/V control membrane. The flux through the composite membrane of this Example was less than that of Example 1 due to the lower hydrogen permeability of the vanadium sulfide layer relative to the $SiO_2$ layer.

EXAMPLE 4

A $Pd/SiO_2/V$ composite metal membrane was made as follows. A vanadium disc, 5 cm in diameter and 30 microns thick, served as the base metal, while a 25-micron-thick palladium foil served as the coating material. A thin layer of $SiO_2$ served as the intermetallic diffusion barrier. The $SiO_2$ layer was deposited on one surface of each of two 5-cm-diameter pieces of Pd foil by first placing a thin film of methanol containing a catalytic amount of HCl on the surfaces of the Pd, then, before the methanol/HCl evaporated, adding $Si(OMe)_4$ dropwise until each of the Pd surfaces was entirely covered; this yielded a thin ($\leq 25$-micron) $SiO_2$ layer by hydrolysis of the $Si(OMe)_4$ due to reaction with atmospheric moisture. The two pieces of $SiO_2$-coated Pd foil were placed $SiO_2$ layer down on both sides of the vanadium disc. The entire assembly was then placed directly in a permeation test cell and laminated in situ during permeation testing at 700 C using the gas feed-pressure of 100 psi (690 kPa) to achieve lamination. The average hydrogen flux through the composite membrane was measured under the same conditions as in Example 1 for nearly six hours and was observed to have stabilized after about two hours at 25.3 $m^3/m^2 \cdot hr$. This high flux is a result of using palladium as the coating metal, rather than nickel or nickel/copper alloy, which has a greater permeability to hydrogen than do nickel or nickel/copper alloys. Even after 50 hours' operation, the flux through the membrane remained constant at 25.3 $m^3/m^2 \cdot hr$, demonstrating that the membrane retained 100% of the initial flux.

For comparison, the average hydrogen flux through a control membrane made by laminating the same thickness of palladium foil directly to the same thickness of vanadium foil without the use of an intervening $SiO_2$ layer was measured under identical conditions. The flux through this control membrane decreased steadily from the initial value of 19 $m^3/m^2 \cdot hr$ to 14 $m^3/m^2 \cdot hr$ after 6 hours, then to 0.91 $m^3/m^2 \cdot hr$ after 50 hours' operation, demonstrating that without the $SiO_2$ layer the membrane retained only 5% of the initial flux. As is apparent, the composite membrane also exhibited higher flux than the Pd/V control membrane.

| Membrane | Flux (initial) | Flux (50 hrs) | % Initial Flux |
| --- | --- | --- | --- |
| $Pd/SiO_2/V$ | 25.3 | 25.3 | 100 |
| Pd/V | 19 | 0.91 | 5 |

EXAMPLE 5

To demonstrate high permeability of the $SiO_2$ layer, a $Pd/SiO_2/Pd$ composite metal membrane was made. Palladium served as the coating metal and the base metal was omitted. Palladium foil, 5 cm in diameter and 25 microns thick, was coated on one side with a thin layer of $SiO_2$ as in Example 4. Another piece of palladium foil of the same dimensions was then placed over the $SiO_2$-coated palladium so that the $SiO_2$ layer was between the two. The assembly was then placed in a permeation test cell and laminated in situ as in Example 5. The average hydrogen flux through the composite membrane, measured under the same conditions as in Example 1, was observed to stabilize at 31 $m^3/m^2 \cdot hr$.

EXAMPLE 6

To demonstrate the high permeability of a $WO_3$ layer for use as a metal-diffusion barrier, a $Pd/WO_3/Pd$ composite metal membrane was made. Palladium served as the coating metal and the base metal was omitted. Palladium foil, 5 cm in diameter and 25 microns thick, was coated on one side with a thin layer of $WO_3$ by applying to one surface a solution of $WCl_6$ in a mixture comprising about 94% methylene chloride, about 5% acetonitrile, and about 1% $Si(OMe)_4$. The $WCl_6$ rapidly hydrolyzed in the presence of atmospheric moisture to yield a thin film of $WO_3$. Another piece of palladium foil of the same dimensions was then placed over the $WO_3$-coated palladium so that the $WO_3$ layer was between two layers of palladium. The assembly was then placed in a permeation test cell and laminated in situ as in Example 4. The average hydrogen flux through the composite membrane was measured under the same conditions as in Example 1 and observed to stabilize at 42 $m^3/m^2 \cdot hr$.

EXAMPLE 7

To demonstrate the high permeability of a $MoO_3$ layer for use as a metal-diffusion barrier, a $Pd/MoO_3/Pd$ composite metal membrane similar to that of Examples 5 and 6 was made as follows. Palladium foil, 5 cm in diameter and 25 microns thick, was coated on one side with a thin layer of $MoO_3$ by applying to one surface a solution of $MoCl_5$ in the same solvent mixture as in Example 6. The $MoCl_5$ rapidly hydrolyzed in the presence of atmospheric moisture to yield a thin film of $MoO_3$. Another piece of palladium foil of the same dimensions was then placed over the $MoO_3$-coated palladium so that the $MoO_3$ layer was between the two pieces of palladium. The assembly was then placed in a permeation test cell and laminated in situ as in Example 4. The average hydrogen flux through the composite membrane was measured under the same conditions as in Example 1 and was observed to stabilize at 67 $m^3/m^2 \cdot hr$.

EXAMPLE 8

A Ni/MoO$_3$/Cu composite metal membrane was made as follows. A copper disc, 5 cm in diameter and 250 microns thick, served as the base metal, while a 25-micron-thick nickel foil served as the coating material. A thin layer of MoO$_3$ served as the metal diffusion barrier, and was deposited on one surface of each of two pieces of 5-cm-diameter nickel foil as in Example 7. The two pieces of MoO$_3$-coated nickel foil were placed MoO$_3$-side down on both sides of the copper foil. The entire assembly was then placed directly in a permeation test cell and laminated in situ during permeation testing as in Example 4. Average hydrogen flux under the same conditions as in Example 1 through the composite membrane was measured and observed to stabilize at 0.37 m$^3$/m$^2$·hr. This flux is identical to that through a copper membrane (250 microns thick, 5 cm diameter) under the same conditions of temperature and hydrogen pressure. Therefore, as expected, the copper base-metal layer is the limiting factor in the overall flux through this composite membrane.

EXAMPLE 9

Pd/Y$_2$O$_3$/V composite metal membranes were made using the following procedure. Vanadium foil 25 μm in thickness served as the base metal, while palladium foil of the same thickness served as the coating metal. A thin layer of Y$_2$O$_3$ was deposited on both sides of the vanadium foil by dropwise addition of an aqueous/methanolic solution containing yttrium isopropoxide [Y(OC$_3$H$_6{}^i$)$_3$] in toluene with HCl as a hydrolysis-promoting catalyst. The Y(OC$_3$H$_6{}^i$)$_3$ rapidly hydrolyzed in a 70% relative humidity bath, forming a thin film on the vanadium. Liberation of excess solvent and condensation of hydroxides to oxides was achieved by heating, under a flow of Argon, the Y$_2$O$_3$·xH$_2$O-coated vanadium foil a 450° C. for one hour. The Y$_2$O$_3$-coated vanadium foil was covered with Pd and laminated in situ under 100 psi (690 kPa) Argon at 700° C. for two hours.

Average hydrogen flux through the Pd/Y$_2$O$_3$/V membranes was 16 m$^3$/m$^2$·hr measured under the same conditions as in Example 1.

The composite metal membranes maintained 100% of the initial average hydrogen flux throughout the 13-day experiment. These data indicate that the Y$_2$O$_3$ layer imparts membrane stability as compared to the non-barrier-containing Pd/V membrane and as compared to a NiO-barrier containing Pd/NiO/V membrane (see Comparative Example).

COMPARATIVE EXAMPLE

A Pd/NiO/V composite metal membrane was made as follows. Vanadium foil 25 μm thick served as the base metal, while Pd foil of the same thickness served as the coating metal. A thin layer of Ni(OH)$_2$ was deposited on both sides of the vanadium from a suspension of Ni(OH)$_2$ in a basic (pH=12) aqueous solution. The vanadium foil/Ni(OH)$_2$ coating was heated at 450° C. in an Argon atmosphere, condensing hydroxide to oxide and liberating excess water. Each side of the coated foil was covered with the Pd foil and laminated in situ under 100 psi (690 kPa) Argon at 700° C. for two hours.

Average hydrogen flux through the composite membrane was measured in the same manner as in Example 1. The initial hydrogen flux was 11.3 m$^3$/m$^2$·hr. After operating for nearly four days, the flux had decreased to 0.6 m$^3$/m$^2$·hr, representing 5% of the initial flux. This result indicates that the NiO layer of the Pd/NiO/V composite metal membrane does not yield a membrane that exhibits stable hydrogen flux. Indeed, the Pd/NiO/V composite metal membrane is no more stable with respect to H$_2$ flux than is the same membrane without the intermediate NiO layer (see Example 4).

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A nonporous hydrogen-permeable, hydrogen-selective composite metal membrane comprising a hydrogen-permeable base metal and a hydrogen-permeable coating metal separated by a hydrogen-permeable intermetallic diffusion barrier selected from the group consisting of oxides of aluminum, lanthanum, molybdenum, silicon, tungsten and yttrium, and sulfides of molybdenum, tungsten and vanadium.

2. The membrane of claim 1 wherein its performance is characterized by a retention of ≧20% of its initial flux after 100 hours' contact with 99.999% pure hydrogen at 100 psig on the feed side, ambient pressure on the permeate side, and at a temperature of at least 500° C.

3. The membrane of claim 1 wherein said base metal is selected from hydrogen-permeable transition metals from Groups IIIB, IVB, VB, VIIB and VIIIB of the periodic table and alloys containing ≧20 wt % of said metals.

4. The membrane of claim 1 wherein said coating metal is selected from a hydrogen-permeable transition metal and alloy thereof, said coating metal being chemically and physically stable at temperatures of at least 500° C.

5. The membrane of claim 4 wherein said coating metal is selected from the group consisting essentially of the transition metals from Groups VIIB and VIIIB of the periodic table, and alloys containing ≧20 wt % of said metals.

6. The membrane of claim 5 wherein said coating metal is selected from the group consisting essentially of Fe, Mn, Ni, Pd, Pt and Ru.

7. The membrane of claim 1 wherein said diffusion barrier is aluminum oxide.

8. The membrane of claim 1 wherein said diffusion barrier is lanthanum oxide.

9. The membrane of claim 1 wherein said diffusion barrier is molybdenum oxide.

10. The membrane of claim 1 wherein said diffusion barrier is silicon dioxide.

11. The membrane of claim 1 wherein said diffusion barrier is tungsten oxide.

12. The membrane of claim 1 wherein said diffusion barrier is yttrium oxide.

13. The membrane of claim 1 wherein said diffusion barrier is vanadium sulfide.

14. The membrane of claim 1 wherein said base metal is vanadium and said coating metal is an alloy comprising 20 wt % nickel and 80 wt % copper.

15. The membrane of claim 1 wherein said base metal is vanadium and said coating metal is palladium.

16. The membrane of claim 1 wherein said base metal is vanadium and said coating metal is nickel.

17. A method for separating hydrogen from other gases comprising contacting a gaseous feed stream containing hydrogen with the membrane of claim 1 at a temperature exceeding 500° C. and at a pressure on the feed side of said membrane that is elevated relative to the pressure on the permeate side of said membrane, allowing the selective permeation of hydrogen through said membrane, and separating hydrogen that permeates through said membrane.

* * * * *

UNITED STATES PATENT AND TRADEMARK OFFICE
CERTIFICATE OF CORRECTION

PATENT NO. : 5,259,870

DATED : November 9, 1993

INVENTOR(S) : David J. Edlund

It is certified that error appears in the above-indentified patent and that said Letters Patent is hereby corrected as shown below:

Col. 3, line 5: delete "14" second occurrence and insert -- 14' --

Col. 5, line 48: insert -- ° -- after 700

Signed and Sealed this

Sixth Day of September, 1994

Attest:

BRUCE LEHMAN

Attesting Officer     Commissioner of Patents and Trademarks